(12) United States Patent
Goldberg et al.

(10) Patent No.: US 7,384,527 B2
(45) Date of Patent: Jun. 10, 2008

(54) ELECTROPHORESIS APPARATUS AND A PLATE THEREFOR

(75) Inventors: Doron Goldberg, Metala (IL); Zeev Weissman, Herzliya (IL); Menachem Shapiro, Upper Galilee (IL); Shlomo Ruschin, Herzliya (IL)

(73) Assignee: Sensis Ltd, Yam (IL)

( * ) Notice: Subject to any disclaimer, the term of this patent is extended or adjusted under 35 U.S.C. 154(b) by 699 days.

(21) Appl. No.: 10/343,633

(22) PCT Filed: Aug. 1, 2001

(86) PCT No.: PCT/IL01/00717

§ 371 (c)(1),
(2), (4) Date: Jul. 14, 2003

(87) PCT Pub. No.: WO02/10706

PCT Pub. Date: Feb. 7, 2002

(65) Prior Publication Data

US 2004/0007465 A1    Jan. 15, 2004

(51) Int. Cl.
*G01N 27/26*    (2006.01)

(52) U.S. Cl. ............... 204/606; 204/600; 204/603; 204/612; 204/615; 204/616

(58) Field of Classification Search ........... 204/600, 204/603, 606, 612, 615, 616
See application file for complete search history.

(56) References Cited

U.S. PATENT DOCUMENTS

| 4,892,638 A | 1/1990 | Watanabe et al. |
| 4,904,366 A | 2/1990 | Tokita et al. |
| 5,108,179 A | 4/1992 | Myers |
| 6,245,507 B1 | 6/2001 | Bogdanov |
| 2002/0110839 A1* | 8/2002 | Bach et al. .......... 435/7.9 |

FOREIGN PATENT DOCUMENTS

EP    0 626 578    7/1998

\* cited by examiner

*Primary Examiner*—Arun S. Phasge
(74) *Attorney, Agent, or Firm*—Browdy + Neimark

(57) ABSTRACT

The invention provides an electrophoresis apparatus comprising an electrophoretic chamber containing at least on two-plate housing for a sieving matrix, each said at least one two-plate housing consisting of a cover plate and a plate for housing said sieving matrix, wherein said plate includes an optical waveguide array which is characterized by being aligned with respect to a reference direction such as to enable one or more light beams incident on the sieving matrix along said reference direction to be maintained well-confined along said reference direction within any desired length of interaction along the width of said sieving matrix.

19 Claims, 14 Drawing Sheets

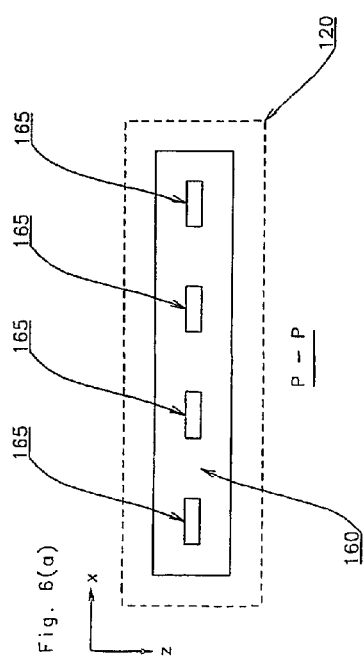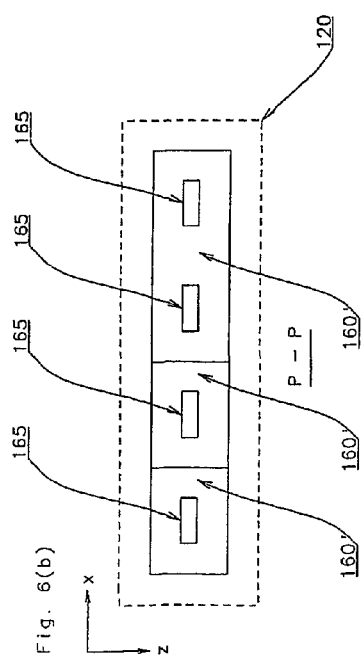

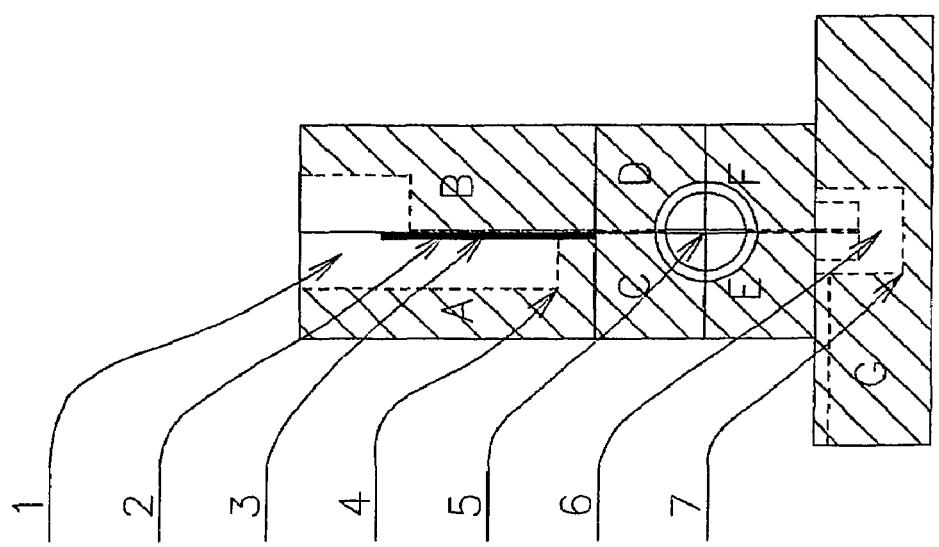

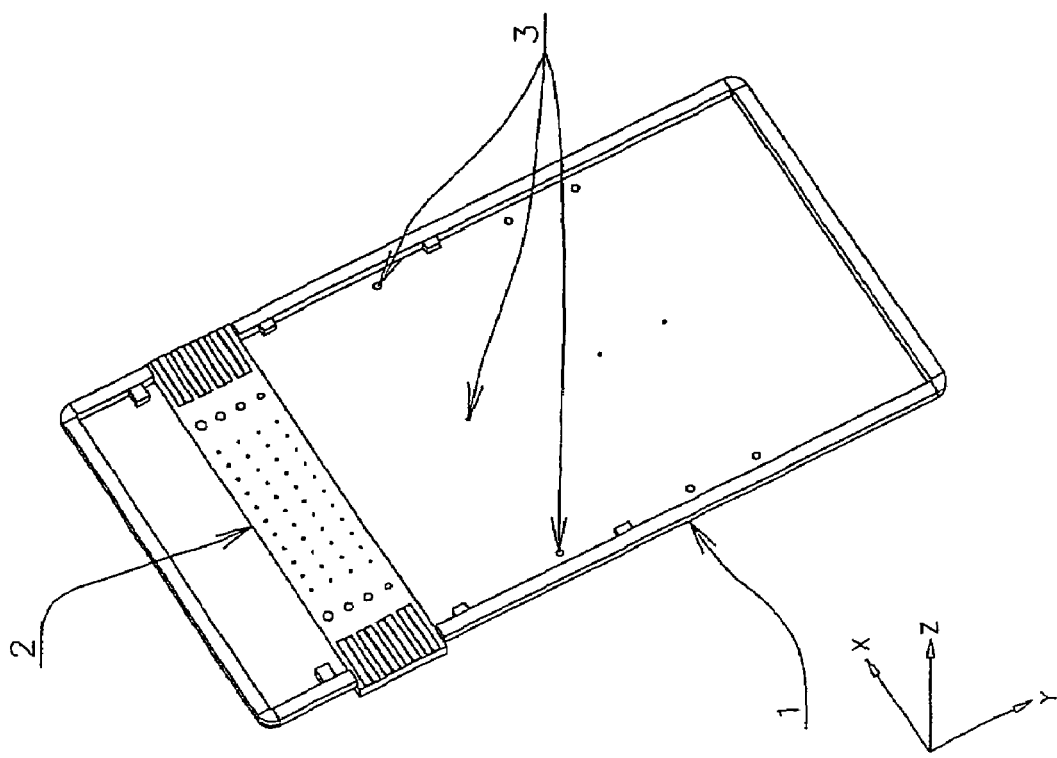

ELECTROPHORESIS APPARATUS AND A PLATE THEREFOR

FIELD OF THE INVENTION

The present invention relates to an electrophoresis apparatus and, in particular, to such an apparatus comprising a plate including at least one waveguide. The apparatus of the present invention is suitable for the detection during electrophoresis of at least one substance in a sample, in particular, peptides, proteins, or nucleic acids, particularly when such substances are present in small amounts in said sample.

BACKGROUND OF THE INVENTION

Electrophoresis, the process whereby charged molecules migrate in an electric field, is often used to separate mixtures of peptides, proteins or nucleic acids. Electrophoresis of proteins is generally carried out in gels made up of the cross-linked polymer polyacrylamide. Samples containing proteins are loaded in wells or depressions at the top of the polyacrylamide gel and the proteins contained in each sample move into the gel in separate lanes when an electric field is applied. The polyacrylamide gel acts as a molecular sieve, slowing the migration of the proteins approximately in proportion to their size, or molecular weight. Polyacrylamide is often used as the gel matrix for short DNAs (up to a few hundred molecules), and agarose is generally used as the gel matrix for separating longer DNA molecules up to the size of the entire chromosomes.

The most common technique for detection of molecules in a slab gel during electrophoresis comprises exciting them with a laser of a suitable wavelength, collecting the ensuing fluorescence and measuring its intensity (Regnier, F. E., He, B., Lin, S. and Busse, J. (1999), "Chromatography and electrophoresis on chips: critical elements of future integrated, microfluidic analytical systems for life sciences", *Trends Biotech.* 17:101-106). In order to use this technique, the electrophoresed molecules should be either capable of emitting fluorescence efficiently, or labeled by another molecule which can do so. While the laser provides a collimated beam of light, a great deal of dispersion or diffraction occurs once within the gel, and therefore the effective cross-section of the beam increases with penetration into the gel to a size considerably larger than at entry thereto, and the intensity is correspondingly reduced. Thus, in order to enable each successive species of molecule that migrates across the laser path to be detected by interaction therewith, it must be ensured that only one such species of molecule at any one time is within the expanded cross-section of the laser beam. Thus, the excitation of the molecules must be conducted at a certain distance from the origin such that the different molecules have already achieved sufficient separation from each other, so that only one type of molecule interacts with the laser beam at any one time. In consequence, the migration length, and therefore the length of the slab gel must be sufficiently long to provide the required separation, which may run, for example, to at least 30 to 50 cm, depending on the gel.

Thus, when the electrophoresis apparatus is adapted for a large slab gel, as in some current DNA sequencing machines, such as in the ALFexpress DNA Analyser® (Amersham Pharmacia Biotech, Uppsala, Sweden), a fixed laser beam is directed into the gel through its side, perpendicular to the direction of the band migration, which excites the fluorescently labeled DNA bands. The resulting fluorescence is then detected by a series of photodiodes (each for each lane) located behind the gel at a right angle to the exciting beam (Sequencing Handbook, (2000), Amersham Pharmacia Biotech, Uppsala, Sweden).

Thus, in the prior art, in order to overcome the problem of laser diffraction within the gel, a rather large sample (having sufficient molecules that are to be detected) must be used, coupled with a sufficiently long gel length to enable the required resolution to be achieved.

However, when the electrophoresis apparatus is a very narrow microfabricated capillary with a cross section of a few tens of micrometers, and the number of electrophoresed molecules is extremely small (typically at the nM range), both the excitation and collection of the emitted photons need to be focused into a tiny volume to minimize background fluorescence and to achieve the required resolution (Mathies, R. A. and Huang, X. C. (1992), "Capillary array electrophoresis: an approach to high-speed, high throughput DNA sequencing", *Nature* 359:167-169). One approach to achieve this has been to employ an external confocal microscope setup, which is placed close to the electrophoresis apparatus (Regnier, F. E., et al, supra). In recent years, the components of capillary electrophoresis (i.e. buffer and sample reservoirs, capillaries, electrodes) have been constantly miniaturized well into the realm of microelectronics (Colyer, C. L., Tang, T., Chiem, N. and Harrison, D. J. (1997), "Clinical potential of microchip capillary electrophoresis systems", *Electrophoresis* 18:1733-1741). Capillary array electrophoresis chips (CAE) which measure 50 mm×75 mm can accommodate many independent microfabricated capillaries and their injection systems (Woolley. A. T. and Mathias, R. A. (1995) "Ultra-high-speed DNA sequencing using capillary electrophoresis chips", *Anal. Chem.* 67:3676-3680.). However, it has been so far impossible to integrate the optical detection system on to the CAE chip, and it has remained a bulky and expensive assembly of external lasers and optical systems (Mathias, R. A., Glazer, A. N., Lao, K. and Wooley, A. T., "Electrochemical detector integrated on microfabricated capillary electrophoresis chips", 1999, The Regents of the University of California, USA). Thus, while this system enables small sample volumes to be used and with relatively short gel lengths, the detection apparatus is large, bulky and relatively expensive and complex.

An alternative method to the above detection scheme is the electrochemical detection of molecules which can be readily oxidized or reduced by electrodes, said electrodes being integrated within an electrophoresis capillary or placed in a close proximity to its end. In comparison with fluorescence detection, electrochemical detection allows for the integration of capillaries and detectors. Electrochemical detection is also very sensitive and can measure quantities as low as $10^{-15}$ mole (Takenaka, S., Uto, Y., Kondo, H., Hiara, T. and Takagi, M. (1994) "Electrochemically active DNA probes: detection of target DNA sequences at femtomole level by high-performance liquid chromatography with electrochemical detection", *Anal Biochem.* 218:436-443). However, this technique is still not widely used, probably because of difficulties in the detection of small currents or voltages in a capillary, which is subjected to many kV during electrophoresis, and also because of the need for very accurate placement and alignment of the electrodes.

Thus, in the prior art, either long gel lengths are required to provide the required resolution, or, alternatively, when short gel lengths are possible, these systems nevertheless require cumbersome and expensive confocal microscopy devices for detection.

SUMMARY OF THE INVENTION

There is therefore a need for, and it is an aim of the present invention to provide, an apparatus for detecting substances in a sample during electrophoresis, particularly when dealing with only small quantities of these substances and when the gel length is kept short.

There is also a need for, and it is another aim of the present invention to provide, an apparatus which is compact, relatively portable, and in which apparatus a plurality of different samples can be electrophoresed simultaneously.

It is another aim of the present invention to provide such a device that incorporates at least one light, e.g. laser, source, at least one light detector and means for processing the data obtained during the electrophoresis, integrally with an electrophoresis chamber.

The present invention achieves these and other aims by providing an electrophoresis apparatus comprising a plate including a waveguide of lenses, hereinafter designated "an optical waveguide" or "a waveguide element".

Thus, in one embodiment, the present invention relates to a plate for housing a sieving matrix for electrophoresis of a sample, said plate including an optical waveguide array, which is characterized by being aligned with respect to a reference direction such as to enable one or more light beams incident on the sieving matrix along said reference direction to be maintained well-confined along said reference direction within any desired length of interaction along the width of said sieving matrix.

The light beam is preferably a laser beam and the sieving matrix is preferably a gel matrix, preferably a gel which is transparent with respect to said incident light, e.g. laser, beams, and is most preferably polyacrylamide or a derivative thereof. The optical waveguide array may contain a sole optical waveguide or a plurality of optical waveguides.

In another embodiment, the present invention relates to a two-plate housing for a sieving matrix for electrophoresis of a sample, comprising a cover plate and said plate including an optical waveguide.

In a further embodiment, the present invention relates to an electrophoresis apparatus comprising an electrophoretic chamber containing at least one two-plate housing for a sieving matrix which comprises a cover plate and said plate including an optical waveguide.

In still a further embodiment, the present invention relates to said electrophoresis apparatus further comprising at least one light source, preferably a laser source.

In still another embodiment, the present invention relates to said electrophoresis apparatus further comprising at least one light detector.

In yet another embodiment, the present invention relates to said electrophoresis apparatus further comprising means for processing the data generated by said at least one light detector.

In yet still another embodiment, the present invention relates to methods for the detection of at least one substance by electrophoresis using an electrophoresis apparatus according to the invention.

BRIEF DESCRIPTION OF THE FIGURES

FIG. 3(a) illustrates results obtained in the detection of yeast proteins by changes in the refractive index of the gel as a function of elapsed time. FIG. 3(b) illustrates results obtained in the detection of DNA fragments by changes in fluorescence as a function of elapsed time.

FIGS. 6(a)-6(b) schematically illustrate alternative cross-sections of the embodiment of FIG. 5 along P-P.

FIG. 9 shows in side elevational cross-sectional view of of an electrophoresis apparatus according to the present invention.

FIG. 13 shows a perspective view of a plate for housing a sieving matrix including an optical waveguide array according to the present invention.

DETAILED DESCRIPTION OF THE INVENTION

Figure 1:
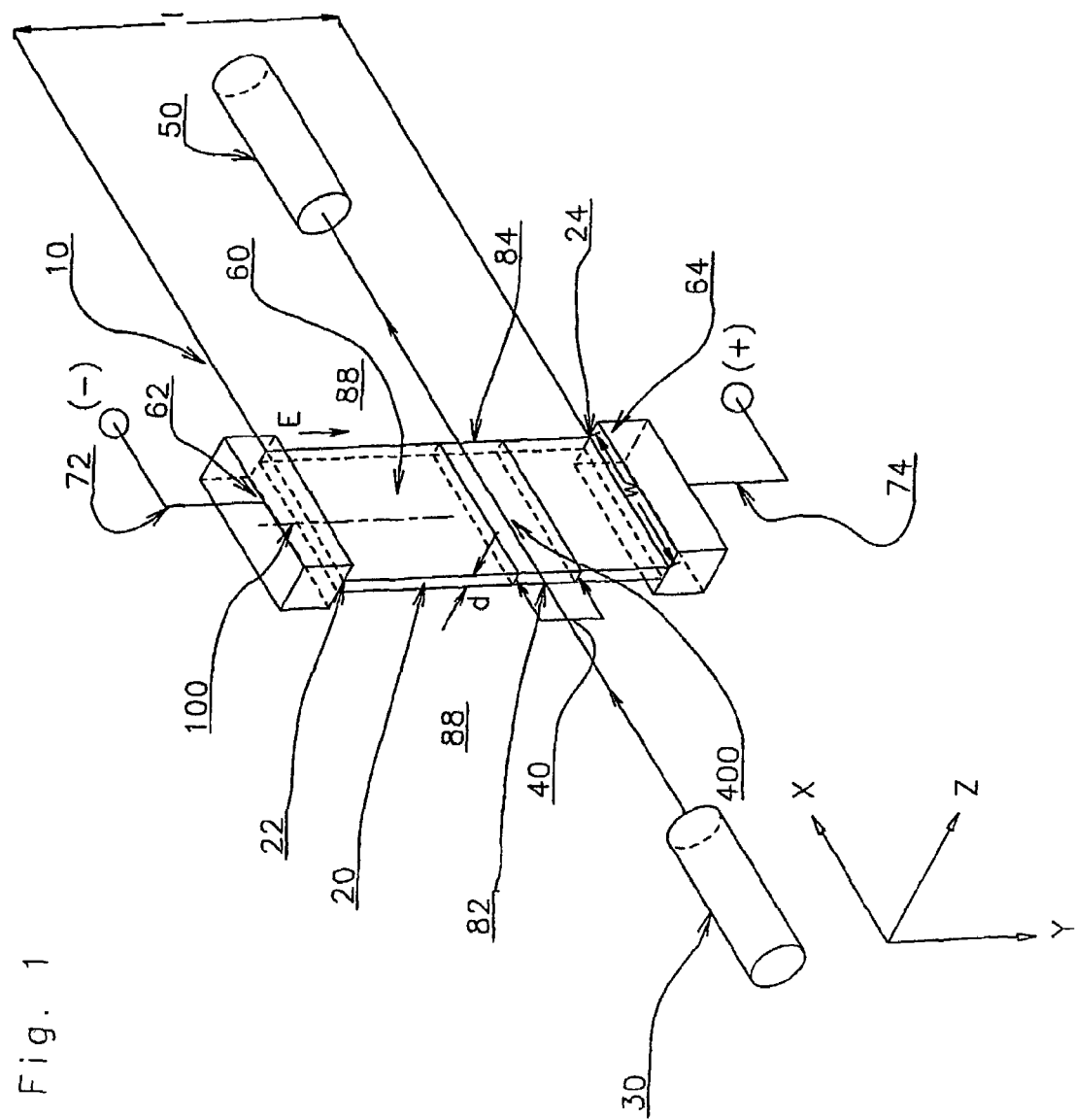
FIG. 1 illustrates schematically the main elements of an electrophoresis apparatus according to the present invention.

The present invention is defined by the claims, the contents of which are to be read as included within the disclosure of the specification, and will now be described by way of examples with reference to the accompanying Figures.

The present invention is directed to a waveguide for use in the detection of at least one substance during electrophoresis in a sieving matrix of at least one sample comprising said at least one substance. The waveguide is characterised in being provided within the sieving matrix, preferably a gel, and in being aligned with respect to a reference direction such as to enable one or more light beams incident on the sieving matrix along said reference direction to be maintained well-confined along said reference direction within at least a desired portion of the sieving matrix.

In a first embodiment, the present invention provides a plate for housing a sieving matrix for electrophoresis of a sample, said plate including an optical waveguide array which is characterized by being aligned with respect to a reference direction such as to enable one or more light beams incident on the sieving matrix along said reference direction to be maintained well-confined along said reference direction within any desired length of interaction along the width of said sieving matrix. It is to be understood that said plate for housing a sieving matrix, as defined herein, is a plate that upon assembly with a cover plate is able to house the sieving matrix.

A sieving matrix, with respect to electrophoresis and as used herein, is a structure of molecular-scale obstacles and pores, which can hinder the motion of charged molecules under the influence of an electric field (Slater, G. W., Desruisseaux, C., Hubert, S. J., Mercier, J -F, Labrie, J., Boileau, J., Tessier, F., and Pepin, M. P. (2000). Theory of DNA electrophoresis: A look at some current challenges. *Electrophoresis* 21: 3873-3887). A sieving matrix can be made of polymers, either linear or cross-linked (i.e. polyacrylamide, agarose, polydimethylacrylamide, etc.), or it can be created by lithographic techniques from silicon, glass or plastic. In traditional chromatographic terms, the sieving matrix of electrophoresis forms the "stationary phase" while the buffer constitutes the "mobile phase". It is the different partition of the electrophoresed molecules between the two phases which makes the resolution of a mixture of molecules into its separate species possible.

In a preferred embodiment of the invention, the sieving matrix is a gel which is transparent with respect to said incident light beams, more preferably polyacrylamide or a derivative thereof such as polydimethylacrylamide.

According to the present invention, the light beam is preferably a laser beam and the plate is preferably made of a plastic material.

The optical waveguide array according to the present invention may contain one sole optical waveguide (one line of at least one lens) or a plurality of optical waveguides (several lines each containing at least one lens).

In one particular embodiment, the optical waveguide comprises at least one lens, herein also called a "waveguiding unit", each said waveguiding unit characterized in enabling diffracted light beam in the sieving matrix along said reference direction, incident with respect to said waveguiding unit, to be refocused along said reference direction, thereby maintaining a well-confined light beam within at least a portion of said sieving matrix along said reference direction. In one preferred embodiment, the optical waveguide comprises a plurality of said waveguiding units aligned in series along said reference direction.

Each waveguiding unit may be a convex-shaped lens, for example, formed as a protrusion or as a fiber optic segment extending in a direction orthogonal to said reference direction. Preferably, said waveguiding unit is substantially cylindrical having a central axis in a direction substantially orthogonal both to said reference direction and to a direction of migration of said sample with respect to said sieving matrix.

In one additional embodiment of the present invention, the light beam incident on the sieving matrix is delivered through at least one optical coupling element located at at least one of the edges of the waveguide, and said light beam delivered though said optical coupling element is collimated by a collimator located before the first waveguiding unit. The optical coupling element is preferably an optical fiber element and the collimator is preferably a convex-shaped lens.

In another aspect, the present invention provides a two-plate housing for a sieving matrix for electrophoresis of a sample comprising a plate according to the invention as described above, and a cover plate. The cover plate may be made of glass or of plastic.

In one embodiment, the two-plate housing according to the invention comprises a precast sieving matrix, preferably a precast gel which is transparent with respect to the incident light beams, more preferably polyacrylamide or a derivative thereof. Precast gels are ready to run, more friendly to the users and the results obtained therewith are more reproducible.

In still another aspect, the present invention provides an electrophoresis apparatus is comprising an electrophoretic chamber containing at least one two-plate housing for a sieving matrix as defined above, each said at least one two-plate housing consisting of a cover plate and a plate for housing said sieving matrix, wherein said plate includes an optical waveguide array which is characterized by being aligned with respect to a reference direction such as to enable one or more light beams incident on the sieving matrix along said reference direction to be maintained well-confined along said reference direction within any desired length of interaction along the width of said sieving matrix.

In one embodiment, the electrophoresis apparatus comprises an electrophoretic chamber that contains one sole two-plate housing, and in particular the electrophoretic chamber may consist of a sole two-plate housing.

In another embodiment, the electrophoresis apparatus comprises an electrophoretic chamber that contains a plurality of said two-plate housings in substantial parallel arrangement stacked along a third direction substantially orthogonal both to a first direction corresponding to the direction of migration of the at least one sample and to a second direction corresponding to the direction of propagation of the light beam.

Thus the present invention encompasses any electrophoresis apparatus which comprises one or more waveguide elements according to the present invention.

The electrophoresis apparatus of the invention may, in addition, comprise any other means necessary for the performance of electrophoresis of samples including, but not being limited to, buffer reservoirs, two electrodes, power supply, light source, light detectors and means for processing the data obtained during electrophoresis of samples.

Thus, in one embodiment, the electrophoresis apparatus of the invention comprises at least one light source, preferably a laser source, for illuminating with a light beam, preferably a laser beam, at least a portion of the sieving matrix in the two-plate housing along a reference direction, herein defined as a second direction, that intersects the direction of the sample migration in the sieving matrix, herein defined as the first direction.

The said at least one light source may comprise means for generating a plurality of light beams. In one embodiment, said plurality of said light beams are modulated such as to prevent temporal overlapping between each said light beam. In another embodiment, said plurality of said light beams are coupled by suitable means to a shared light radiation outlet means for emitting in turn each one of said plurality of said light beams. Each one of said plurality of said light beams is preferably of a substantially different wavelength such as to enable the excitation of different dyes used to label the substances being detected in a sample.

The apparatus may also comprise a plurality of light sources, particularly when it comprises an electrophoretic chamber that contains a plurality of said two-plate housings.

The electrophoresed molecules, particularly labeled molecules, will be detected by the light beams confined by the optical waveguide when they traverse it during an electrophoresis run. The mode of detection of the labeled molecules will be measurement of either absorption of the guided light or fluorescence. Proteins, and possibly other substances, which locally alter the sieving matrix refractive index, can be detected by monitoring the resulting variations in the intensity of the guided light.

Thus, the interaction between the light beam(s) and the substance being detected at a certain portion of the sieving matrix, provides a change in an optical characteristic of that portion of the sieving matrix that can take one of three forms:

detection method (a)—absorbance of the light beam by the substance results in an increase in the absorbance in the sieving matrix and in a decrease of the intensity of the light beam emitting from the sieving matrix, which can be detected by a detector that detects variations of light intensity, e.g. laser intensity;

detection method (b)—fluorescence emitted by the substance due to its excitation by the light beam results in an isotropic increase in the light intensity in the sieving matrix, which can be detected by a detector that detects fluorescent photons;

detection method (c)—interaction of the light beam with the substance and the sieving matrix results in a change in the refractive index of the sieving matrix, resulting in a change of the intensity of the light beam emitted from the sieving matrix, which can then be detected by a detector that detects variations of light, e.g. laser, intensity.

If the detection mode is absorption (method a), an additional light beam, with a wavelength that cannot be absorbed by the labeled molecules, is passed through the waveguide and is used as a reference.

In an additional embodiment, the electrophoresis apparatus of the invention comprises at least one detection means for detecting the change in optical characteristics of the sieving matrix such as at least one light detector, for example a light detector which enables detection of fluorescence photons or variations of light intensity, e.g., laser intensity. Examples of such light detectors include, without being limited to, charge coupled devices (CCD) sensitive for the detection of fluorescence, photodiode or photomultiplier.

In yet another embodiment, the electrophoresis apparatus of the invention further comprises means for processing the data obtained during the electrophoresis. For example, the data can be analyzed by a dedicated computer program which can take the raw data generated by the detector, filter out the signal from the noise, and display the filtered signal as an electropherogram, which is a graph showing, for example, the intensity of fluorescence at the detector with respect to time. The peaks of the electropherogram, which represent the bands of DNA or protein molecules passing the detector, can then be processed by the software to present a DNA sequence or an image of a virtual gel.

In still another aspect, the present invention provides methods for the detection of substances during electrophoresis using an apparatus of the invention as described above.

In one embodiment, there is provided a method for the detection of at least one substance during electrophoresis, which comprises:

(i) loading at least one sample comprising said at least one substance in at least one lane formed by a sieving matrix contained in a two-plate housing according to the invention;

(ii) running said at least one sample in said at least one lane in a first direction with a suitable buffer under a suitable applied electrical potential;

(iii) illuminating the sieving matrix with a light source such that the optical waveguide of the plate comprised within said two-plate housing enables the confining of the light beam along a second direction intersecting said first direction, whereby the interaction between said light beam with said at least one substance provides a change in an optical characteristic of said light beam or of said sieving matrix;

(iv) detecting said change in said optical characteristic with a suitable light detector; and (v) processing the data generated by said detector.

In one embodiment of the above method, said at least one substance is labeled with a suitable dye and the interaction between said light beam with said at least one labeled substance provides an increase in the absorbance in said sieving matrix and the emitted light along said second direction is detected by a light detector which detects variations of light intensity.

In another embodiment of the above method, said at least one substance is fluorescently labeled and the interaction between said light beam with said at least one labeled substance provides an increase in the fluorescence in said sieving matrix and the emitted fluorescence along a third direction is detected by a light detector which detects fluorescence photons.

In a further embodiment of the above method, the interaction between said light beam with said at least one substance and with said sieving matrix provides a change in the refractive index in said sieving matrix resulting in variations of the emitted light intensity which is detected by a light detector.

The methods wherein the substances to be detected are fluorescently- or dye-labeled are suitable, for example, for detecting peptides, proteins, SDS-denatured proteins and nucleic acids. The method wherein the substance is detected by a change in the refractive index of the sieving matrix may be preferably used for the detection of proteins and SDS-denatured proteins.

The invention will now be exemplified with reference to the Figures.

In a first aspect of the present invention, the detection apparatus is adapted for the detection of one or more substances in a single sample. In its simplest form, and referring to FIG. 1, an electrophoresis apparatus of the invention, generally designated as (10), comprises an electrophoresis chamber containing a two-plate housing (20), illumininating means (light source) (30) directed towards a test portion (40) of the two-plate housing (20) along a second direction, and detection means (light detector) (50) for detecting electromagnetic radiation passing through the portion (40) along a third direction, and a waveguide element (400). It is to be understood that as used herein (20) refers to a two-plate housing as well as to an electrophoresis chamber containing a two-plate housing, and (400) refers to a waveguide element also designated optical waveguide herein in the specification and claims.

The two-plate housing (20) comprises longitudinally spaced first and second ends, (22) and (24), respectively, defining a length dimension (1). The two-plate housing (20) comprises a a gel enabling migration of at least one substance of interest (comprised in a sample loaded in a lane formed by the gel) in a first direction from said first end (22) to said second end (24) under a suitable electrical potential (E) therebetween. Said first direction is also parallel to the longitudinal axis (100) of the two-plate housing (20) and may be defined as being parallel to an axis (y) of three mutually orthogonal imaginary axes (x, y, z), as illustrated in FIG. 1, for simplicity of reference.

The two-plate housing (20) has a suitable depth (d) and width (w) (parallel to the (z) and (x) axes, respectively)

suitable for accommodating a suitable slab gel (60) therein for electrophoresis. In this embodiment, the length (1) and width (w) of the two-plate housing are each significantly larger than the depth (d) of the gel accommodated in the plate (20). In another embodiment, though, it is possible for the depth to be of the order of, or indeed greater than the width of the two-plate housing. Such a slab gel (60) may comprise, for example, polyacrylamide gel, particularly if said apparatus (10) is used for vertical gel electrophoresis. The housing is typically designed to enable the gel to be poured thereinto, and subsequently removed therefrom when required, preferably in a simple manner, and thus the plate containing the gel and the cover plate may be designed in a way that they can be joined together and dismantled as required.

As part of the electrophoresis system, the gel (60) comprised in the plate (20) is in ionic communication, and typically also in fluid communication, with buffer solutions contained in buffer reservoirs (62), (64) at the said first end (22) and said second end (24), respectively. Preferably, the buffer reservoirs (62), (64), are integrated with the two-plate housing or with the electrophoretic chamber containing said housing(s) at opposed longitudinal ends thereof Also as part of the electrophoresis system, the buffer reservoirs (62), (64) at the said first and second ends, (22), (24) respectively, are in electrical communication with at least one cathode (72) and at least one anode (74), respectively. As with the buffer reservoirs (62), (64), the cathode (72) and the anode (74) are preferably integrated with the apparatus (10) and are electrically connectable to an external (or integral) DC power supply or equivalent to enable the electric potential (E) to be established between the said first end (22) and the said second end (24).

In this embodiment, the electrophoresis two-plate housing (20) comprises at least one first portal (82) optically co-aligned along a second direction with at least one opposed second portal (84), the first portal (82) and the second portal (84) being typically integrated in the housing. While typically only one such first portal (82) and one such second portal (84) are usually necessary, the apparatus (10) may optionally comprise a plurality of each said portal (82), (84). The portals (82), (84) are thus on opposite sides of the housing (20) and provide optical communication between said housing (20) and an outside (88) of said housing (20) along the said second direction. The said at least one first portal (82) and said at least one second portal (84) are located intermediate said first and second ends (22), (24). In particular, the portals (82), (84) are situated at the test portion (40) of the housing (20). The said second direction intersects said first direction, and in the case of multiple electrophoresis lanes (used for a multiplicity of samples), each said first direction corresponding to and aligned along corresponding lanes also intersect with the second direction when a single illuminating means is provided for the plurality of lanes, as discussed in more detailed hereinbelow for another embodiment. Preferably the second direction is orthogonal to the said first direction, in FIG. 1 the second direction being substantially parallel to the (x) axis and thus along the width of the gel (60), i.e., co-aligned with the electrophoresed bands. Thus, the portals (82), (84) may comprise transparent windows made from any suitable transparent material such as glass or PMMA, for example, on the housing. If the housing itself is made from a transparent material, then the portals (82), (84) are part of the housing at the transverse ends (i.e., along the (x) direction) of the test portion (40). The outside (88) referred herein with respect to the housing (20) may be the outside of the housing itself, or may also constitute the space between the housing (20) and the illuminating means (30) or the detection means (50).

The illumination means (30) are for illuminating with a suitable light, preferably a laser beam, at least a portion, typically the said test portion (40), of said electrophoresis housing (20) between said first portal (82) and said second portal (84) along said second direction via said first portal (82). At least part of said laser radiation exits this test portion (40) of the housing (20) via said at least portal (84) in a third direction, herein being substantially co-aligned with the said second direction. In this type of arrangement, detection methods (a), (b) or (c) may be used for detecting the sample. However, in other embodiments, at least part of the laser radiation may exit the second portion along a third direction which is different from the second direction, notably orthogonal to the first and second axes, i.e., parallel to the z-direction, as described hereinbelow. In particular, when using method (b), the sample is visibly detectable in directions other than along the second direction when irradiated by the laser beam, since the sample's fluorescence is radiated in directions other than just along the second direction. The illumination means (30) comprises a laser generator, typically a laser diode, capable of producing one or a plurality of laser beams, or alternatively a number of laser diodes each producing a laser beam. In the first aspect of the present invention, only one laser beam is generally required. In the second aspect of the present invention, more than one laser beam may be required, in which case they may be coupled via an optical coupler to a collimator. Preferably, the illumination means (30) forms an integral part of the apparatus (10), and is conveniently easily mountable and dismountable therefrom for maintenance purposes, for example. The illumination means (30) is preferably aligned along the said second direction, i.e., parallel to the x-axis, but other arrangements are possible including any required optical components to finally direct the laser beam into the gel via portal (82) along the second direction. Typically, laser diodes having emission wavelengths compatible with the absorption wavelength of a usable dye material may be suitable for the apparatus (10). Such a dye material is typically highly absorptive (i.e., having a high extinction coefficient), easily linked to DNA molecules and suitable for gel electrophoresis (i.e., not too bulky to hinder migration of electrophoresed molecules). For example, a laser diode that emits a laser wavelength of about 650 nm is compatible with the fluorescent dye Cy5 (Amersham Pharmacia Biotech, Uppsala, Sweden), and is therefore suitable for the apparatus (10).

Said detection means (50) are for detecting the change in the laser radiation after interaction with the substance being detected, as received in a third direction. In this embodiment, the said third direction is substantially coaligned with the second direction. Thus, the detection means (50) detect via said second portal (84) the portion of said laser radiation exiting said test portion (40) of said housing (20). Typically, the detection means comprises a charge coupled device (CCD) camera or a suitable photodiode detector that is particularly sensitive to changes in the intensity of the laser radiation received thereat from the test portion (40) via second portal (84). Typically the detection means (50) is operatively coupled to a suitable recording system, particularly capable of real-time recording, preferably a computer. The manner in which detection of the substance of interest may be accomplished is described in detail hereinbelow.

The device (10) further comprises at least one waveguide element (400) for maintaining the laser beam substantially collimated within at least a portion of the gel containing at least the substance being detected, and this portion must also be sufficient to include, when appropriate, a plurality of substances derived from multiple samples electrophoresed in parallel lanes. The expression "maintained collimated" with respect to the laser beam within the gel is herein taken to mean that the laser beam is confined within a diffraction envelope that is substantially parallel to the second direction, regardless of whether the laser beam is itself exactly collimated within the envelope or whether the laser beam is diffracted and then refocused within the envelope, once or repeatedly in cycles.

Figure 2:
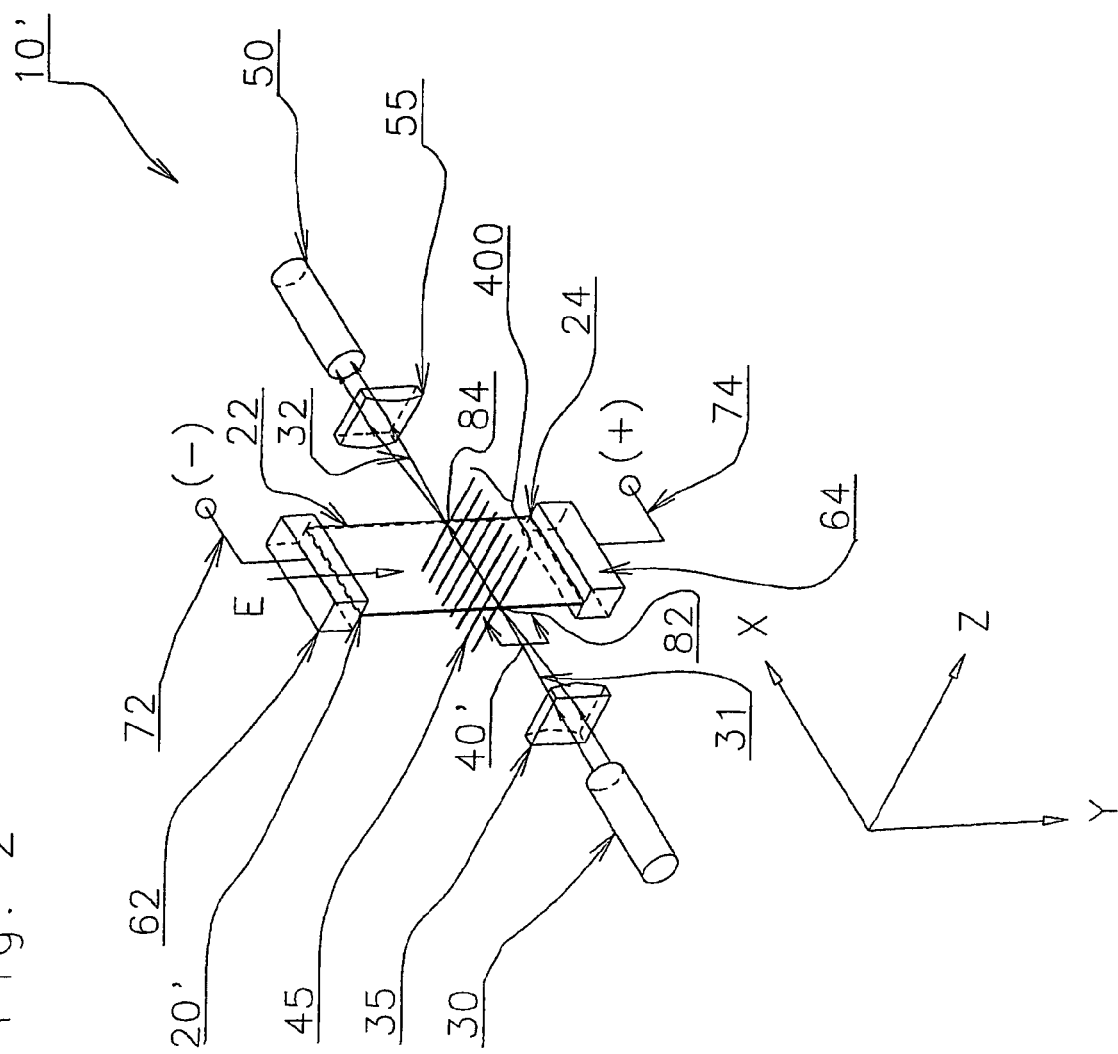
FIG. 2 illustrates schematically the main elements of an electrophoresis apparatus showing the waveguide element according to the present invention.

Another embodiment of the present invention, also according to the first aspect thereof, is schematically illustrated in FIG. 2, and comprises the same structural elements as the first embodiment, with the exception of the said housing (20) and said test portion (40), and in particular the waveguide elements (400), as hereinbefore described, mutatis mutandis. In the present embodiment, the apparatus (10') comprises a housing (20') having a test portion (40'), both of which are significantly wider than the Rayleigh distance $z_0$ of the incident beam when using either detection method (a) or method (b).

The Rayleigh distance $z_0$ may be defined as $$z_0 = \pi W^2 n / 4\lambda$$

where W is the width of the beam, n is the refractive index of the gel, and $\lambda$ is the vacuum wavelength of the laser beam.

In the present embodiment, the at least one waveguide element (400) is embedded within the gel and is thus distinct and separate from the substance being detected, which nonetheless may also have waveguiding properties. The waveguide elements (400) are typically permanently disposed along the second direction for any given gel sample. Thus, in the present embodiment, the at least one waveguide element (400) may comprise at least one and, typically, a plurality of waveguiding units (45) arranged in series along the principal axis of the laser beam provided by the illuminating means (30) along the second direction (typically parallel to the (x)-axis) and located in the test portion (40'). The waveguiding units (45) thus serve to periodically refocus the laser beam, typically at critical locations along the second direction (with spacings less than the Rayleigh distance $z_0$) as the beam travels through the gel, and thus maintains confined the laser beam. This counteracts the diffraction effects of the gel when its width is greater than Rayleigh distance $z_0$—such larger width being provided for increasing the spatial resolution and the signal/noise ratio of the laser transmission received by the detection means, and is also useful in accommodating multiple electrophoresis lanes, further described hereinbelow with respect to a second aspect of the present invention.

In the present embodiment, each waveguiding unit (45) comprises a substantially cylindrical focusing element arranged with its central axis orthogonal to both the first direction (along the direction of electrical potential (E)) and the second direction (the principal axis of the laser beam within the gel), i.e., parallel to the (z) axis or along the depth dimension (d) of the gel. Each waveguiding unit (45) is typically made from a glass fiber suitably mounted within said test portion (40'), having a diameter of between about 120 μm to about 130 μm, and preferably about 125 μm, although different diameters to this may also be acceptable. The refractive index of such waveguiding units (45) is about 1.48, and that of a typical polyacrylamide gel in which it is typically immersed is about 1.34, and this combination allows the laser light travelling along the second direction from the illumination means (30) to be refocused in this direction to counter the diffraction effects of the gel on the laser beam as it passes therethrough, thereby maintaining collimated (confined) the laser beam within the gel. The laser beam spans essentially the full depth of the waveguiding units (45), and is thus wide enough such that negligible diffraction occurs over the propagating distance of the beam. As the width of the housing (20') is increased, the number of waveguiding units (45) increases proportionately. In the schematic example illustrated in FIG. 2, eight waveguiding units (45) are aligned along the path of the laser beam (31). Alternatively, the waveguiding units (45) may be formed as lens-shaped protrusions produced from any suitable optically transparent material. For example, such protrusions may be produced from silicon by chemical etching. These protrusions project into the housing (20') and may be integrally formed with at least part of the housing (20'). In any case, each waveguiding unit comprises at least one principal axis, which is substantially aligned with the said reference direction.

As illustrated in FIG. 2 for the present embodiment, the illuminating means (30) may optionally further comprise a hemi-cylindrical focusing element (35) for converting the laser beam from a substantially circular transverse cross-section to a substantially elliptical transverse cross-section having its major axis parallel to the z-direction and aligned with the central axes of the waveguiding units (45), thereby maximising the focusing effect of the waveguiding units (45).

The apparatus (10') according to the present embodiment of the present invention may be used for the detection of at least one substance in a sample using any one of detection methods (a), (b) or (c) described hereinabove.

Figure 3A:
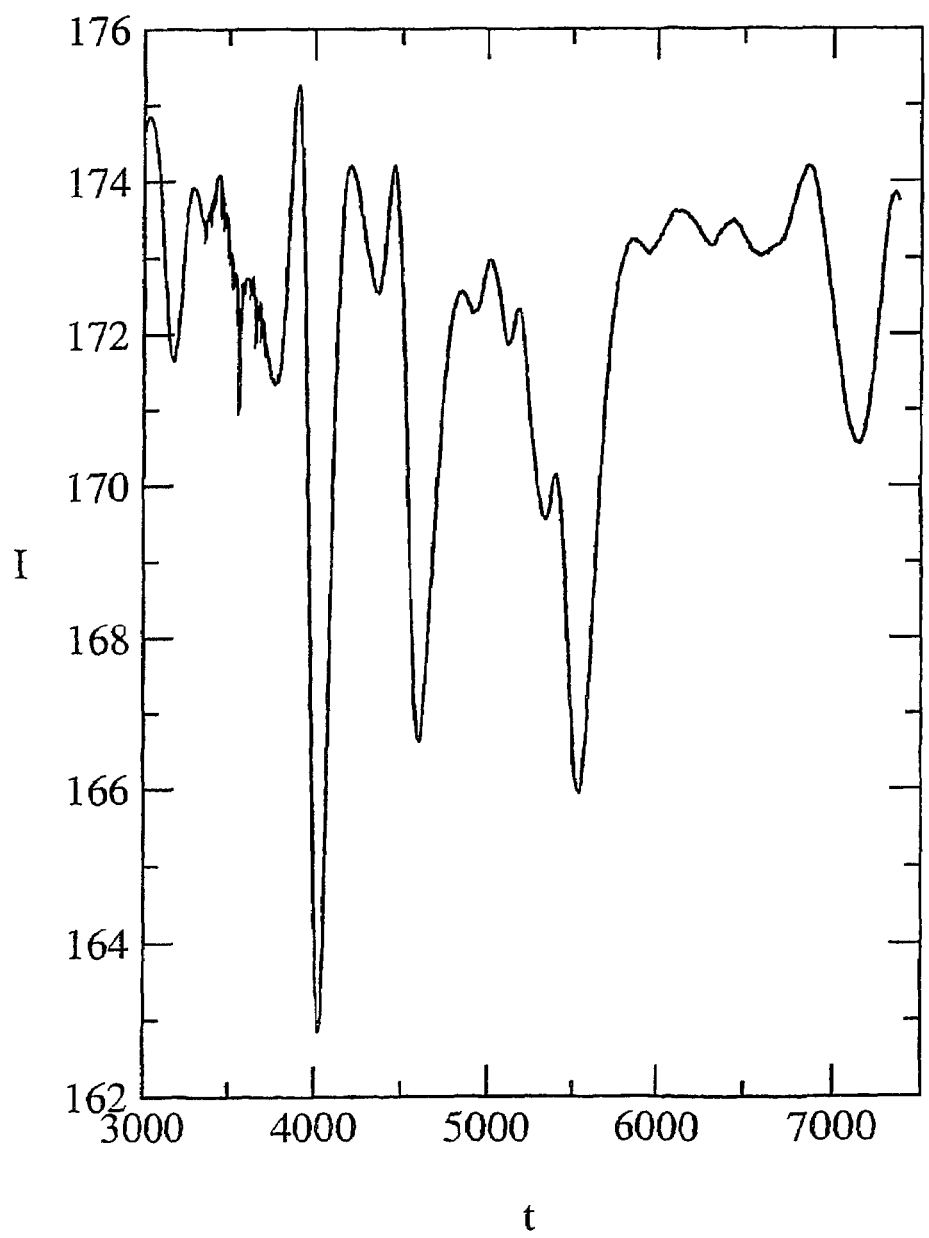
FIGS. 3a-3b are graphs depicting results obtained by detection methods according to the present invention.

Starting first with method (c), the apparatus (10') according to the present embodiment of the present invention may be operated as follows: Proteins electrophoresed in denaturing polyacrylamide gels alter the refractive index of the gel locally, i.e., in the region close to the proteins. This property of proteins enables the use of the apparatus (10') for the detection of proteins in a manner that does away with the need for labelling the same. Since the efficiency by which light is guided by the waveguiding units (45) is dependent on the difference between the refractive index of the elements (45) and that of its surroundings, i.e. the gel, the elements (45) need to be sensitive to the passing of protein bands past the same along the y-direction, even when the proteins are not labelled. The inventors used the test apparatus described in the EXAMPLE section hereinbelow to detect 10 μg total yeast proteins electrophoresed in a standard SDS denaturing polyacrylamide gel with a length of 1.5 cm. The results obtained are shown in FIG. 3(a) as the intensity (I) of the laser radiation received over a predefined region of interest with respect to elapsed time (t) in seconds. This region may be defined graphically on the image of the laser beam exiting the waveguides and the outlet portal (84). This image is captured by the detection means (50), typically a CCD, and displayed on a computer screen. Each pixel of the image corresponds to a pixel of the CCD and has a digitised value ranging from 0 to 255, proportional to the laser intensity of the received laser transmission (32) at the detection means (50). The stronger the intensity, the higher the value associated with the CCD pixel over time. The results obtained by Elliott (Eliott, A. (1979) "The Instantaneous Monitoring of Polyacrylamide Gels During Electrophoresis", Biochem J., 159:743-748) and the results shown in FIG. 3(a) demonstrate the viability of using the apparatus (10') of the present invention for the detection of proteins during polyacrylamide gel electrophoresis.

It should be noted that when using the apparatus (10') of FIG. 2 in detection method (c), the SDS-denatured proteins may actually cause a diffraction of the laser beam through the gel, because the refractive index of the waveguide elements (45) is generally greater than that of the protein bands, and thus the protein bands may be detected as a reduction in laser intensity received at the detection means (see EXAMPLE). This set up is therefore in some ways similar to method (a) in terms of the type of results that are ultimately obtained.

The apparatus (10') may also be used according to detection method (b)—fluorescence—as follows: For DNA sequencing, the purpose of the apparatus (10') may be to identify the base type (A, C, G or T) of each DNA band that crosses the path of the laser beam (31) generated by the illumination means (30). For simplicity, the identification of a single DNA base (say, A) will first be described. The sensing or detection mechanism of the apparatus (10') is based on propagating a narrow laser beam along the width of the slab gel (typically a distance of about 2 cm), i.e., along the DNA bands and therefore substantially parallel to the x-axis. To resolve 500 base pairs over a longitudinal gel length of about 3 cm, the required resolution is better than 3 cm/1000, i.e., 30 µm. To maintain such width of the laser beam over a propagation length (i.e. width of gel or chamber (20')), the waveguiding units (45) are required, for example as herein described.

Figure 4:
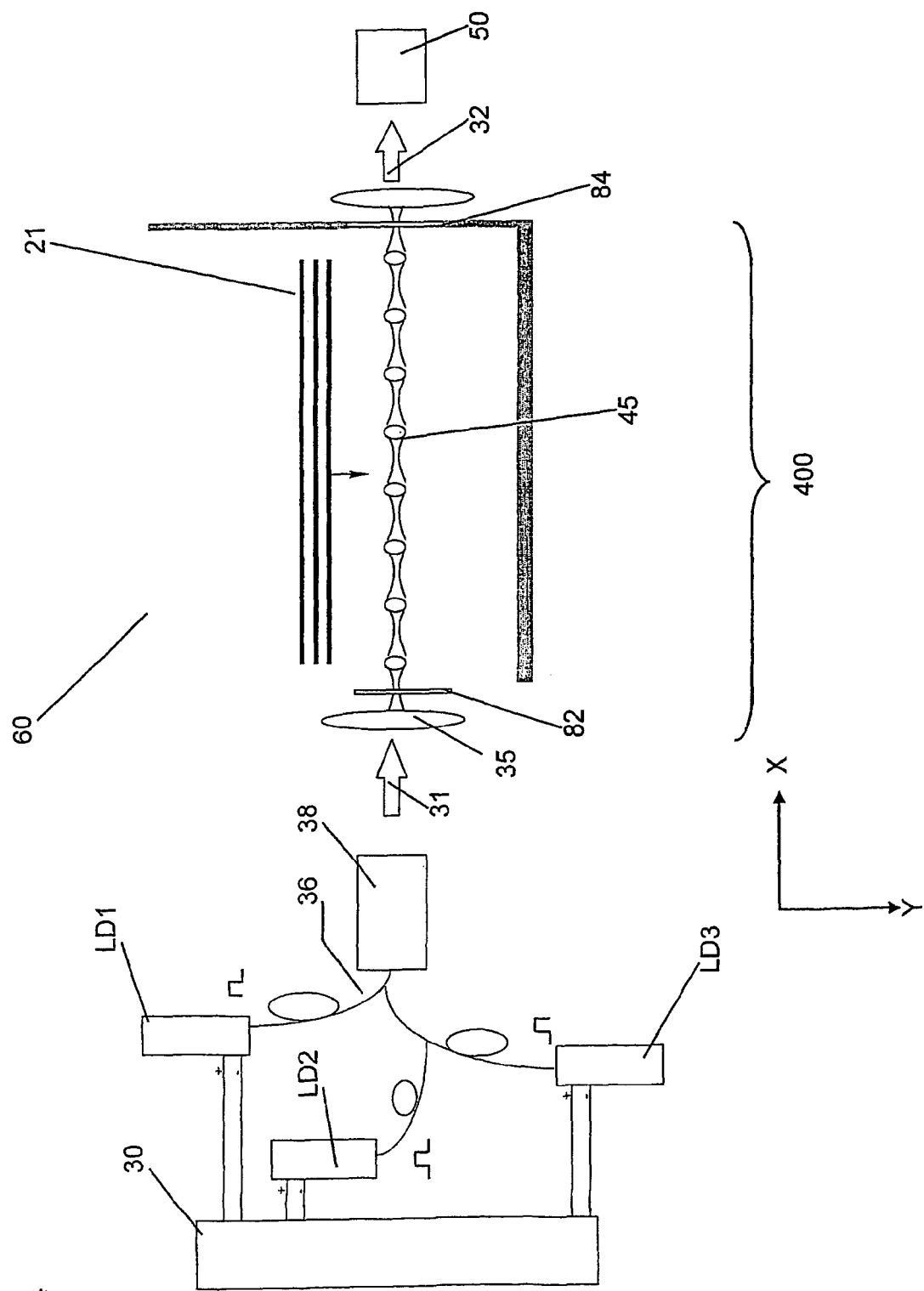
FIG. 4 shows in side elevational partial cross-sectional view of the embodiment of FIG. 2 comprising a plurality of laser beams coupled via an optical coupler.

Referring in particular to FIG. 4, there are eight waveguiding units (45) comprised in the focusing means, for example. Waveguiding simulations conducted by the inventors indicate that for spacings between adjacent said elements (45) of about 2.4 mm, the beam height along the y-axis oscillates about a mean value of about 18 µm, which provides the resolution required for identifying the DNA bands.

The wavelength of the laser beam generated by the illuminating means (30) is chosen to match the peak absorption wavelength of the fluorescent dye that is used for labelling the respective DNA nucleotides. For example, the fluorescent dye Cy5 (Amersham Pharmacia Biotech, Uppsala, Sweden) has an absorption maxima at 649 nm, and laser diodes that emit at 649 nm (the standard wavelength for current digital video disk (DVD) applications) is suitable. When a Cy5-labelled DNA band passes through the path of the laser beam, in particular as refocused by the waveguiding units (45), the dye molecules in the DNA band (A) partially absorb the laser beam energy; and (B) fluoresce at a slightly longer wavelength (670 nm, in this example). By detecting the absorption (A) or the fluorescence (B), the presence of the DNA nucleotide of type A can thus be detected by the detection means (50).

When the apparatus (10') is used to detect and to distinguish between each of the four DNA nucleotides, A, C, G and T, the DNA strips (21) need to be color-coded. This may be achieved by using a four-colour coding process, but may also be achieved more economically by using a combinatorial code of two or of three colors. While the following desciption is concerned with the detection method using two colors, the corresponding methods for three or four color coding will be clear to a skilled man of the art. Referring once again to FIG. 4, the optical arrangement in the illumination means (30) comprises three laser beams that are aligned with the waveguiding units (45). Two of these laser beams are used for the detection of the presence of the two fluorescent dye markers used in this example. Thus, if markers Cy5 and Cy7, for example, are used, the relevant wavelengths of the two laser beams (31) are 649 nm and 743 nm, respectively, generated by laser diodes (LD1) and (LD2), respectively. The third laser beam (for example at 690 nm) is used for reference to improve measurement sensitivity and is generated by a third laser diode (LD3). The three beams are first coupled into a shared optical fiber (36) and then emitted into the test portion (40'), in particular the waveguiding units (45), via a collimator (38). The reference wavelength is poorly absorbed by either one of the two labelling dyes, yet it is close enough to the other two wavelengths to be refocused by the focusing means and thus guided by the waveguiding units (45). During operation of the apparatus (10'), the three laser beams are modulated in sequence, with a 1:3 duty cycle, so that there is no temporal overlapping between the three beams, i.e., not more than one of the beams is transmitted through the test portion (40') at any given instant. The resulting laser beam intensities measured by the detection means (50) are processed and outputted as the ratios of each one of the intensities of first two laser beams to that of the reference laser beam. This ratio is sensitive to the crossing of the respective DNA bands, while at the same time being compensated for non-specific optical effects in the apparatus (10') such as mechanical fluctuations in the coupling system, for example. Two-color coding can be implemented by labelling each of the four types of nucleotides. For example, one possible color combination using the two dyes Cy5 and Cy7 which can be excited by laser wavelengths of 649 nm and 743 nm, respectively, may be as follows:

| Type of Nucleotide | Fraction of Cy5 label | Fraction of Cy7 label |
| --- | --- | --- |
| A | 1 | 0 |
| C | 0 | 1 |
| G | 0.666 | 0.333 |
| T | 0.333 | 0.666 |

The apparatus (10') of the present invention described above may be also used according to detection method (a)—absorption—in a similar manner as described above with respect to detection method (b), mutatis mutandis. In other words, the detection means (50) detects a drop in the intensity of the received laser beam whenever a band of substance to be detected interacts with the refocused beam provided by the waveguiding units (45). The different bands of nucleotides can be identified by time-demultiplexing the time-multiplexed dual-wavelength beam. In other words, the drop in intensity at a certain combination of illuminating laser wavelengths indicates a respective color-coded band type.

The apparatus (10) according to the first aspect of the present invention when used in particular with proteins according to detection methods (a) or (b), the proteins are labelled with a suitable dye.

In a second aspect of the present invention, the detection apparatus is adapted for the detection of at least one substance in each one of a plurality of samples. Each of the plurality of samples may be provided in the same gel or in a plurality of gels in parallel arrangement, or in sets of pluralities of gels in parallel arrangement.

Figure 5:
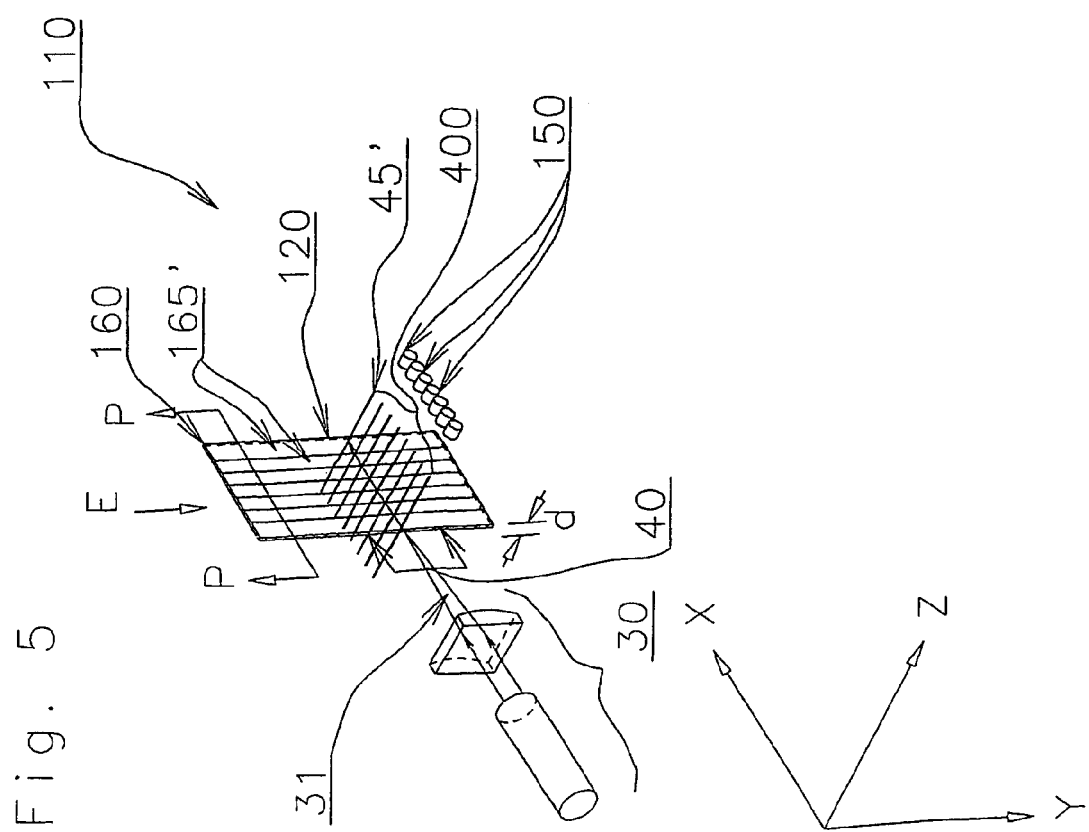
FIG. 5 illustrates schematically the main elements of an electrophoresis apparatus according to the present invention adapted for the detection of substances in a plurality of samples and comprising a plurality of detection means corresponding to the plurality of samples.

In a second aspect of the present invention, schematically illustrated in FIG. 5, the apparatus comprises the same structural elements as above, with the exception of the said electrophoresis chamber or housing (20) and the detection means (50), as hereinbefore described, mutatis mutandis. In the present embodiment illustrated in FIG. 5, the apparatus (110) is adapted for the detection of one or more substances in each of a plurality of samples carried by a single slab gel (160). The slab gel (160) thus comprises a plurality of parallel electrophoresis lanes (165) corresponding to each sample, wherein each lane (165) may be relatively narrow, typically in the order of about 3 mm to 5 mm, as illustrated in FIG. 6(a). Alternatively, but arguably less practical, the apparatus (110) may be adapted for the detection of one or more substances contained in each one of a plurality of samples, wherein each sample is comprised on a separate slab gel (160') stacked in parallel arrangement along the second direction (parallel to the (x)-axis), in which each gel slab (160') comprises one (or more) electrophoresis lanes (165), as before, as illustrated in FIG. 6(b). As such, the electrophoresis chamber (120) according to the present embodiment may be considerably wider (along the x-direction) than for the previous embodiment.

In the present embodiment, the apparatus (110) comprises a plurality of detection means (150), corresponding to the plurality of samples, and thus comprises one detection means (150) per lane (165). For simplicity, FIG. 5 only shows the slab gel (160), illumination means (30), focusing elements (45') and detection means (150). This embodiment is typically used in conjunction with detection method (b), i.e., fluorescence.

Still according to the present embodiment, the detection means (150) are arranged to detect the change in the laser radiation in a third direction which is substantially perpendicular to the first direction and parallel to the depth dimension (d) of the gel sample (160). In other words, the detection means can detect an increase in the light intensity in the gel radiated along the third direction due to irradiation of the fluorescent substance by the laser beam, which is maintained collimated (confined) via the waveguide elements (400). Thus, each detection means (150) is aligned parallel to the z-axis with its corresponding lane (165), and directed at the test area (40) of the sample, as illustrated in FIG. 5. The waveguiding units (45') are provided such as to ensure that all of the lanes (165) are simultaneously excited via the illumination means (30). Thus, for any given lane (165), as each labelled substance therein migrates along the first direction (substantially parallel to the y-axis) and crosses the path of the laser radiation (emitted along a second direction, substantially parallel to the x-axis), the increase in the fluorescence of the test area (40) corresponding to this lane (165) is detected by the corresponding detection means (150), along the third direction (substantially parallel to the z-axis). When more than one substance is to be detected in each lane (165), the illuminating means may comprise a collimator arrangement and detection may be carried out in a similar way to that described above, mutatis mutandis, with the difference of course that the detection is in a third direction perpendicular to the original path of the laser beam, rather than aligned therewith.

Figure 7:
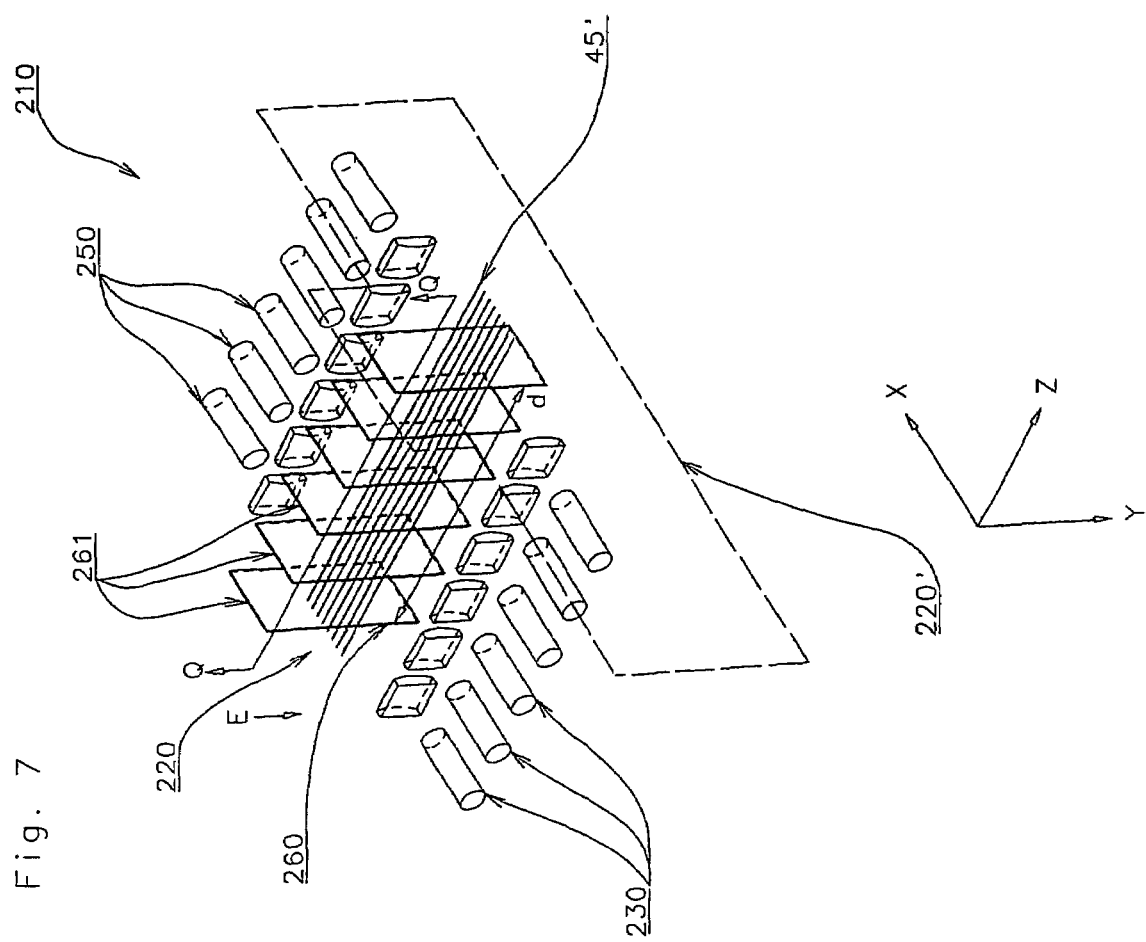
FIG. 7 illustrates schematically the main elements of an electrophoresis apparatus according to the present invention comprising a plurality of slab gels.
Figure 8A:
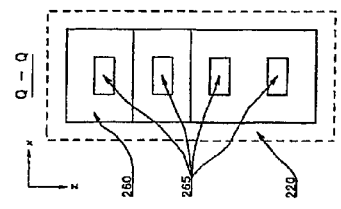
FIGS. 8(a) to 8(d) schematically illustrate alternative cross-sections of the embodiment of FIG. 7 along Q-Q.
Figure 8B:
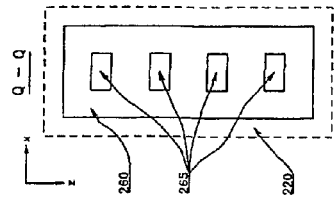

A further embodiment of the present invention, also according to the second aspect thereof, is schematically illustrated in FIG. 7, and comprises the same structural elements as above, mutatis mutandis, with a number of exceptions as follows. In the present embodiment, the apparatus (210) is adapted for the detection of one or a plurality of substances contained in each of a plurality of samples applied to one or a plurality of slab gels (260) in parallel arrangement stacked or spaced parallel to the z-axis. Thus, in lieu of the chamber (20) of previous embodiments, the electrophoresis chamber (220) of the present embodiment is adapted to accommodate therein the one or plurality of slab gels (260). As illustrated in FIG. 8(a), an electrophoresis lane (265) is provided for each sample, which may comprise one or a plurality of substances to be detected. Alternatively, and as illustrated in FIG. 8(b), the slab gel (260) may be comprised of discrete slab strips (261), each of which may accommodate one or more of the electrophoresis lanes (265). In this embodiment, the electrophoresis chamber has a relatively greater depth (d) than that of the previous embodiments. Further, rather than having a single illumination means (30) and detection means (50), there is a dedicated illumination means (230) and detection means (250) associated with each of the samples contained in the gel (260), providing a plurality of illumination means (230)/sample/detection means (250) sets. The illumination means (230) and detection means (250) are respectively similar to the illumination means (30) and detection means (50) of the previous embodiments as described above, mutatis mutandis. On the other hand, the focusing elements (45) preferably extend the full depth (d) of the chamber (220) in a similar manner to that of the previous embodiments. For simplicity, FIG. 7 only shows the plurality of samples in parallel gel slices or strips (261) with their associated illumination means (230) and detection means (250), as well as the focusing elements (45').

In this present embodiment, each illumination means (230)/sample/detection means (250) set operates as an independent detection cell (220') for the detection of one or more substances comprised in the corresponding sample. In each cell (220') the corresponding detection means (250) are arranged to detect the change in the laser radiation in a third direction which is substantially aligned with the first direction. The present embodiment is typically used in conjunction with detection method (a), i.e., absorbance, but it may also be readily used in conjunction with detection method (b) or with detection method (c). In fact, since the cells (220') are essentially independent one from the other, some cells (220') may be operated using method (a), other cells (220') with method (b) and yet other cells (220') with method (c), in any desired permutation.

Figure 8C:
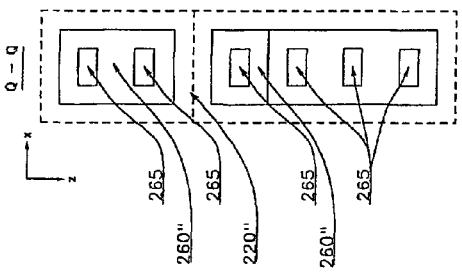
Figure 8D:
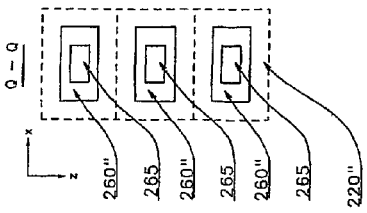

Alternatively, the apparatus may comprise a plurality of individual electrophoresis chambers (220") in place of the single chamber (220). As illustrated in FIGS. 8(c) and 8(d), wherein each such chamber (220") may be adapted for accommodating one or more samples along the x-axis, and comprised in corresponding electrophoresis lanes (265) which may be comprised in a gel (260"). The gel (260") may be, for each chamber (220"), either integral or comprised of a plurality of gel slices and/or strips in appropriate parallel arrangement.

While the cross-sections of the lanes (165) and (265) in FIGS. 6 and 8 have been represented as rectangular, any other suitable cross-section may be used, including for example, polygonal, circular or elliptical.

The apparatus of the present invention and corresponding methods of operation thereof thus offer a high degree of integration of a sensitive yet simple optical detector and a miniaturized polyacrylamide gel, or any other sieving matrix with similar properties, for electrophoresis of samples. The small dimensions of the detector's guided light endows it with high resolving power of bands which may be only 50 micrometer wide and approximately 50 micrometer apart, thus taking full advantage of the excellent resolution of different molecular species, by the polyacrylamide gel electrophoresis, which can be achieved after a very short run of merely several centimeters. Further, the apparatus also offers flexibility in the selection of the preferred detection method, since it can be used to detect either absorbency, fluorescence or variation in the refractive index. The relatively simple design of the proposed apparatus and the integrated two-plate housing for the sieving matrix (slab gel) enables mass production of small units which can then be combined to form arrays of any desired size.

The apparatus and methods according to the present invention are suitable for any slab gel electrophoresis in which dye-labeled molecules have to be separated and detected. However, it is particularly directed to high speed, cheap DNA sequencing, both for genetic testing and for research purposes.

Figure 10:
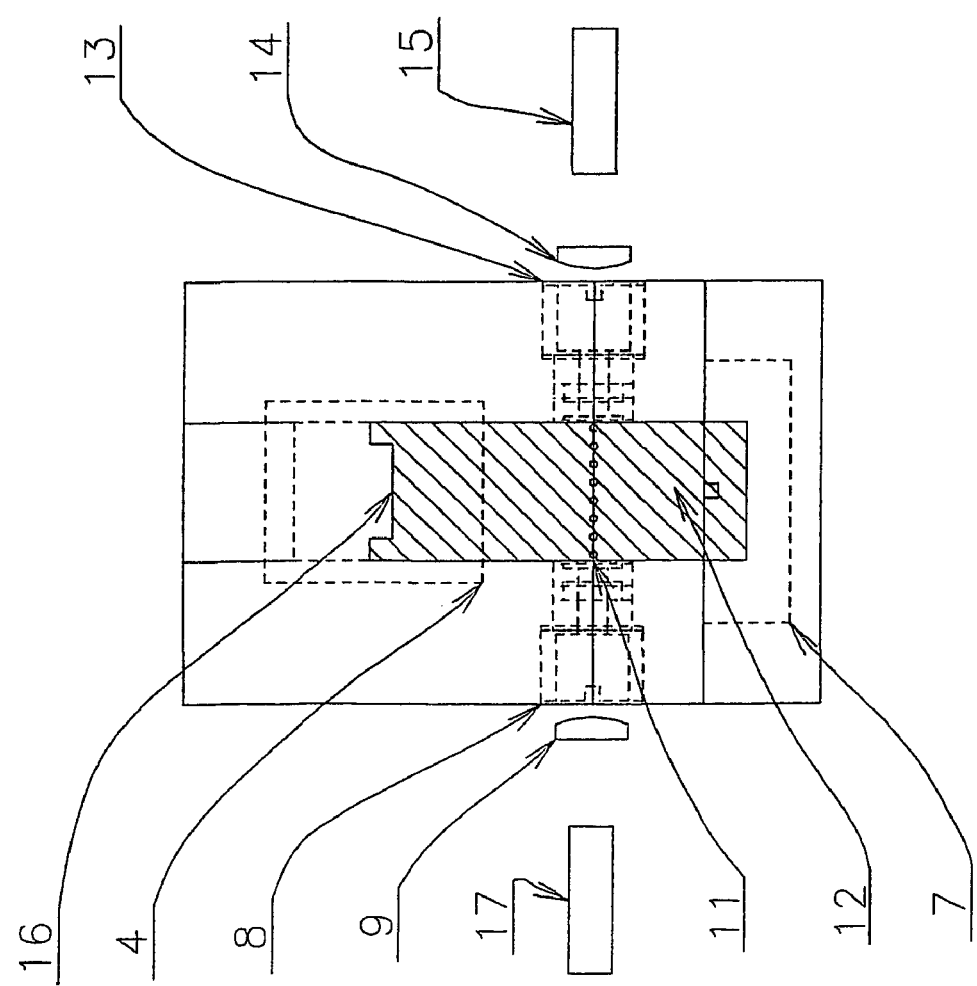
FIG. 10 shows in front elevational cross-sectional view of the embodiment shown in FIG. 9.
Figure 11:
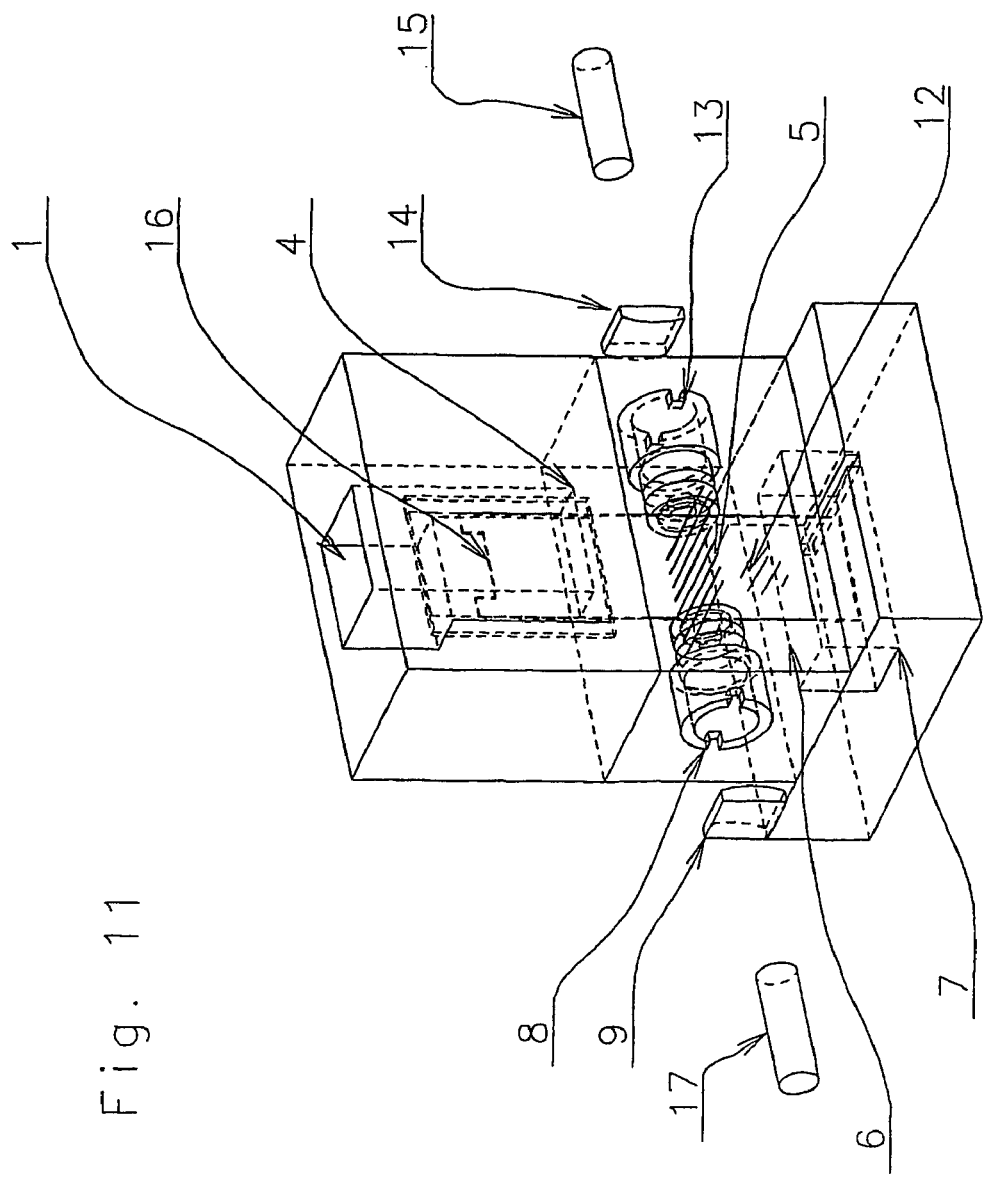
FIG. 11 shows partially hidden and partially exposed perspective view of the embodiment shown in FIGS. 9 and 10.

FIGS. 9-11 depict an apparatus of the present invention containing an electrophoresis chamber with an integrated detector, that was fabricated from several pieces of acrylic (Perspex). The 0.4 mm-wide gel cell was formed by joining together two machined acrylic blocks, (A), (B) each with a depression of 0.2 mm×8 mm×1.5 cm. In one of the blocks, the depression was formed by covering the upper buffer reservoir (1) (which comprises cathode (4)) with a microscope slide, 0.2 mm below the block's surface. The glass wall (3) of the cell (2) and its contact with the buffer during electrophoresis ensured better and even heat dissipation. The detector was fabricated in a similar manner, but this time by joining together two pairs of machined acrylic blocks, (C), (D), (E) and (F). In each pair, the blocks had a 0.2 mm deep depression that formed the lower part of the gel cell (adapted for accommodating gel (12), see FIG. 10) when the blocks were glued together (FIG. 9). The first pair (C), (D) formed the upper part of the detector, and the second pair (E), (F), its lower part. Eight grooves were engraved on the surface of the lower part to house eight cylindrical lenses (5) made of ordinary optical fibers each 2 cm long and with a diameter of 0.125 mm (FIGS. 10, 11). The optical fibers were perpendicular to the gel and traversed it. Two holes were drilled opposite each other on both sides of the waveguide to form housings for two glass windows—one window (8) for the light entry into the gel, and one window (13) for its exit (FIGS. 10,11). Places of contact between the different parts where the polymerizing gel could leak, were sealed by injecting a silicone sealer into special grooves. The gel cell (2) and the detector were screwed on an acrylic base, which contained the lower buffer chamber (6) and anode (7) (FIG. 9).

The laser source of the apparatus is a laser diode with a wavelength of 657 nm, coupled to an optical fiber with a mini collimator in its end (iFLEX-1000, Point Source, England). As illustrated in FIG. 10, the collimator (17) itself was mounted on a special 6-axis translator-rotator behind a coaxial cylindrical lens (9) (10×10 mm; 25 mm focal length; CASIX, China), which focused the laser beam on the first lens (11) of the waveguide. The 6-axis translator-rotator allowed for the essential accurate illumination of the waveguide. The light emitting from the waveguide was collected by a second cylindrical lens (14) mounted on a similar 6-axis translator-rotator, and a monochromatic CCD camera (15) (WAT902B; Watec, Japan) positioned behind it. The camera output was sampled at 50 Hz with a 32 bit board (DT3155; Data Translation, Massachusets, USA) controlled by an in-house program written for the SDK frame grabber software (Data Translation, Massachuset., USA) running on a 450 MHz Pentium III PC. For measurements of fluorescence, an avalanche photodiode (APD) module (C5460-01-SPL-BW1K, Hamamatsu Photonics, Hamamatsu City, Japan) was mounted on the transparent electrophoresis chamber, perpendicular to the waveguide. The detection of stray laser light was prevented by mounting a cylinder with three notch filters (XF3076, Omega Optical, Vermount, USA) spaced at 2.5 cm intervals, in front of the APD. The APD output was sampled at 1 kHz with a 16-bit A/D board (KPCI-3107, Keithley Instruments, Ohio, USA) controlled by a LabVIEW virtual instrument (VI) running on a 450 MHz Pentium III PC.

Figure 12:
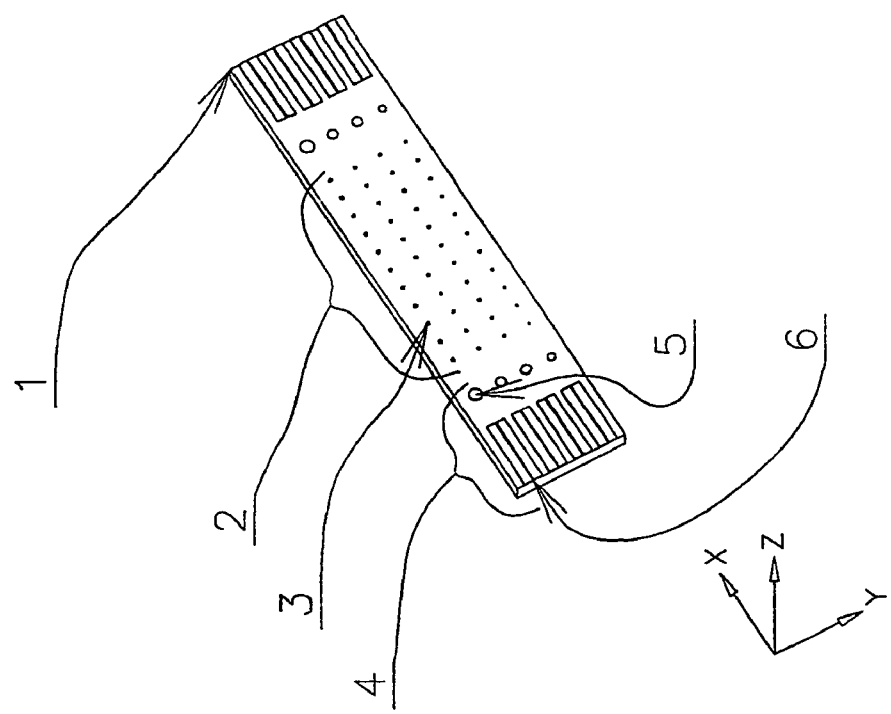
FIG. 12 shows a perspective view of an optical waveguide array according to the present invention.

FIG. 12 shows a perspective view of an optical waveguide array (1) made of plastic constituting one preferred embodiment according to the invention, which includes four optical waveguides (2), each of them comprising eleven waveguiding units (3). Each optical waveguide is flanked by two light couplers (4), each light coupler including a cylindrical lens (5) and a groove for an optical fiber (6).

FIG. 13 shows a perspective view of a plate for housing a sieving matrix (1) made of plastic with the integrated optical waveguide array (2) described in FIG. 12, constituting one preferred embodiment according to the invention. The plate carries several protrusions (3) which act as spacers between the plastic plate and a cover glass or plastic plate (not shown).

In addition to the figures described above, the invention will now be illustrated by the is following non-limiting Examples.

EXAMPLES

Example 1

Electrophoresis of Proteins in SDS-polyacrylamide Gel (i) Preparation of Total Yeast Proteins Dehydrated yeast (0.05 gr) were lysed in an Eppendorf tube containing 0.3 gr glass beads and 1 ml lysis buffer (50 mM MES pH 6.0, 0.1 mM $MgCl_2$, 0.1 mM EGTA, 1 mM β-mercaptoethanol, and 2 mM PMSF). After 5 min of vortexing, the lysate was transferred to a new tube, and centrifuged (1000 rpm; 1 min). The supernatant was collected and ¼ volume loading buffer (40% glycerol, 12% SDS, 0.2 M Tris pH 6.8, 20% β-mercaptoethanol, and 0.01% bromophenol blue) was added. The cell lysate containing total yeast proteins was boiled for 3 min, and then placed on ice until loading.

(ii) Electrophoresis

Total yeast proteins were electrophoresed in 12% SDS-polyacrylamide gel using the method of DISC-PAGE as follows: 2 ml of 12% acrylamide running gel solution were prepared by mixing 0.8 ml 30% acrylamide/0.8% bisacrylamide, 0.5 ml 1.5 M Tris-HCl pH 8.8, and 0.7 ml DDW. Two ml of 4% acrylamide stacking gel were prepared by mixing 0.26 ml 30% acrylamide/0.8% bisacrylamide, 0.5 ml 0.5 M Tris-HCl pH 6.8, and 1.24 ml DDW. The gel solutions were filtered through a 0.2 μm pore size filter. Polymerization was initiated by adding to the running gel solution 10 μl of 10% freshly-prepared ammonium persulfate, and 2 μl TEMED (N,N,N,N-tetramethylethylenediamine). After mixing, about 0.3 ml of the polymerizing gel solution was quickly poured into the two-plate housing until it was full up to 10 mm below the top. A layer of DDW was then laid on top of the gel to allow even polymerization of the gel edge. After the running gel had been polymerized, the water layer was removed, and about 0.1 ml of polymerizing stacking gel were added on top of the running gel. A 0.4 mm spacer was then inserted into the cell to form a single-well 8 mm-wide, and the stacking gel was allowed to polymerize. After the gel had been polymerized, the buffer chambers were filled with running buffer (0.3% Tris, 1.44% glycine, and 0.1% SDS), the well-forming spacer was removed and the well was washed with running buffer. Ten μl sample were loaded into the well. The run was started with the power supply set a limiting value of 50 V and stopped after 120 min.

(iii) Results and Discussion

The results of the electrophoresis of SDS-denatured proteins are shown in FIG. 3(a). In this run we used a waveguide element made of 8 optical fibers. Each peak marks a reduction in the intensity of the laser beam, which is caused by the passage of a protein band, with a higher refractive index, through the waveguide.

This experiment demonstrates that detection of proteins during their electrophoresis is feasible, even without the need to label them. In standard electrophoresis techniques, proteins which run in a polyacrylamide gel are usually visualized by their staining with special stains at the end of the electrophoresis run. The staining process is often tedious, and may take up to a day to complete. Only when the gel is stained it can be imaged and analysed. These disadvantages of the prior art can be overcome with the present invention. By using the waveguide of the present invention, electrophoresed proteins can be detected during the run-time and not after finishing the running and staining the sel. The data obtained, such as those shown in FIG. 3(a), can be converted by suitable means into an instant image of a gel, in which variations of light intensity are represented by different colors. For example, by using different hues of blue, a digital image will very much resemble any ordinary Coomassie blue-stained gel. Analysis of such image, which is already stored digitally, can be carried out by a dedicated software as soon as the electrophoresis is over.

Example 2

DNA Sequencing (i) Preparation of Labeled DNA Sequencing Fragments

One of the methods for DNA sequencing makes use of a fluorescently labeled primer, to which the nucleotides are added according to the sequence of the template DNA. If the primer is labeled with various fluorescent molecules, each colored primer can be assigned to a different nucleotide, and the DNA sequence of the fluorescently-labeled fragments can be then determined. In the present example the template for the DNA sequencing reaction was a single-stranded pUC18 plasmid DNA, and the primer was M13 reverse primer, labeled with the fluorescent molecule Cys5. The Cys5-labeled DNA sequencing fragments were produced by means of the ALFexpress AutoCycle sequencing kit (Pharmacia Biotech) using ddATP in a PCR-like reaction essentially according to the manufacturer's manual (Pharmacia B., ALF express Auto Cycle sequencing Kit, 1999, Pharmacia Biotech, Uppsala, Sweden). The products of 10 identical reactions with ddATP were pooled together, precipitated, and resuspended in 6 μl of DDW (double-distilled water) and 4 μl of stop solution containing 100% deionized formamide, and blue dextran (5 mg/ml).

(ii) Electrophoresis

Two ml of gel solution (100 mM Tris, 83 mM boric acid, 1 mM EDTA, 7 M urea, 5% Long Ranger™ (FMC, Rockland, Me.)) were filtered with a 0.2 μm pore size filter. Polymerization was initiated by adding 2 μl 25% freshly-prepared ammonium persulfate and 2 μl TEMED (N,N,N,N-tetramethylethylenediamine) to the gel solution. After mixing, about 0.5 ml of the polymerizing gel solution was quickly poured into the two-plate housing until it was completely full. A 0.4 mm spacer was then inserted into the gel solution to form a single-well 8 mm-wide, and the gel was allowed to polymerize for 1 hr at room temperature. After the gel had been polymerized, the buffer chambers were filled with 1×TBE running buffer (100 nM Tris, 83 mM boric acid, 1 mM EDTA), the well-forming spacer was removed, and the well was washed with the running buffer. A single sequencing reaction was heated for 2 min at 95° C., and immediately placed on ice. 10 μl of the sample were withdrawn and loaded into the well. The run was conducted with the power supply set a limiting value of 2 W, and stopped after 20 min.

(iii) Results and Discussion

Figure 3B:
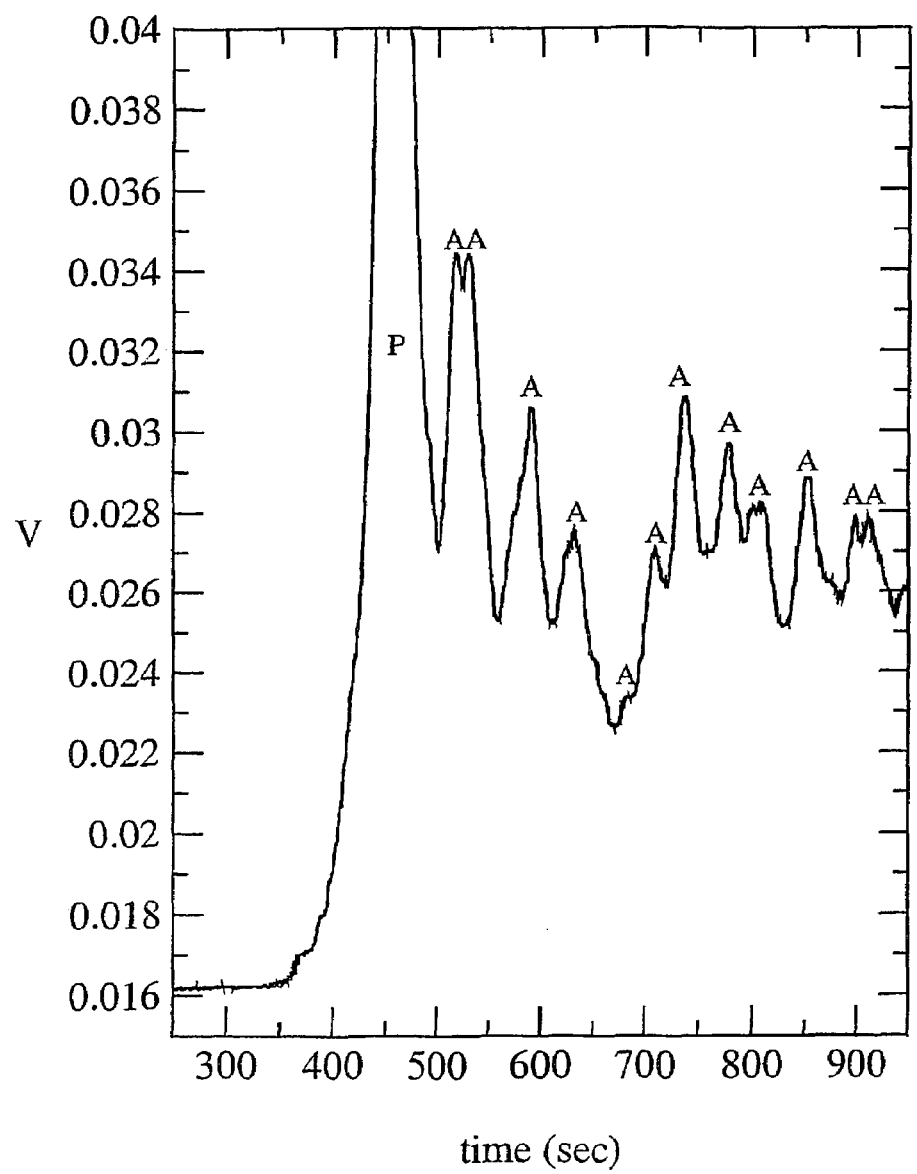

The results of the electrophoresis run of the Cys5-labeled DNA fragments are shown in FIG. 3(b). Twelve peaks of photodiode output voltage, which represent 12 Adenine residues, are clearly seen. The complete sequence which includes these 12 bases is:

```
201 ACACAGGAAA CAGCTATGAC CATGATTACG AATTCGAGCT CGGTACCCGG
251 GGATCCTCTA GAGTCGACCT GCAGGCATGC AAGCTTGGCA CTGGCCGTCG
```

The sequenced residues are bold and underlined. The numbers are the original sequence coordinates of the template plasmid pUC18. The letter P marks the position of the sequencing primer. The peaks of the photodiode output voltage, shown in FIG. 3(b), clearly demonstrate that the fluorescently-labeled DNA fragments can be detected during electrophoresis using the waveguide element. Similarly, four different fluorescent molecules (one for each of the four bases Adenine, Cytosine, Guanine, and Thymine), and four laser sources irradiating at different wavelengths can be used to detect all the fluorescently-labeled DNA fragments (containing the four different ddNTP). This method, therefore, enables a fast and complete DNA sequencing during electrophoresis of a sample.

While this description illustrates in detail only a few specific embodiments of the invention, it will be understood by those skilled in the art that the invention is not limited thereto and that other variations in form and details may be possible without departing from the scope and spirit of the invention herein disclosed.

The invention claimed is:

1. A plate for housing a sieving matrix for electrophoresis of a sample, said plate including an optical waveguide array within the sieving matrix, said optical waveguide array being adapted to focus and/or refocus a laser beam, and being characterized by being aligned with respect to a reference direction such as to enable one or more laser beams incident on the sieving matrix along said reference direction to be maintained well-confined along said reference direction within any desired length of interaction along the width of said sieving matrix.

2. A plate according to claim 1, wherein said optical waveguide array contains one sole waveguide.

3. A plate according to claim 1, wherein said optical waveguide array contains a plurality of waveguides.

4. A plate according to claim 1, wherein said optical waveguide comprises at least one waveguiding unit, each said waveguiding unit characterized in enabling diffracted laser beam in the sieving matrix along said reference direction, incident with respect to said waveguiding unit, to be refocused along said reference direction, thereby maintaining a well-confined laser beam within at least a portion of said sieving matrix along said reference direction.

5. A plate according to claim 1, wherein at least one said waveguiding unit comprises at least one convex-shaped lens.

6. A plate according to claim 1, wherein said one or more laser beams incident on the sieving matrix are collimated by a collimator located before the first waveguiding unit.

7. A plate according to claim 6, wherein said collimator is a convex-shaped lens.

8. A two-plate housing for a sieving matrix for electrophoresis of a sample comprising a plate according to claim 1, and a cover plate.

9. An electrophoresis apparatus comprising:
(i) an electrophoretic chamber containing at least one two-plate housing for a sieving matrix, each said at least one two-plate housing consisting of a cover plate and a plate for housing said sieving matrix, wherein said plate includes an optical waveguide array within the sieving matrix, wherein said optical waveguide is adapted to refocus a laser beam and which is characterized by being aligned with respect to a reference direction such as to enable the laser beam incident on the sieving matrix along said reference direction to be maintained well-confined along said reference direction within any desired length of interaction along the width of said sieving matrix;
(ii) at least one laser source; and
(iii) at least one light detector.

10. An electrophoresis apparatus according to claim 9, wherein said optical waveguide array contains one sole waveguide.

11. An electrophoresis apparatus according to claim 9, wherein said optical waveguide array contains a plurality of waveguides.

12. An electrophoresis apparatus according to claim 9, wherein each said optical waveguide comprises at least one waveguiding unit, each said waveguiding unit characterized in enabling diffracted laser beam in the sieving matrix along said reference direction, incident with respect to said waveguiding unit, to be refocused along said reference direction, thereby maintaining a well-confined laser beam within at least a portion of said sieving matrix along said reference direction.

13. An electrophoresis apparatus according to claim 12, wherein at least one said waveguiding unit is a convex-shaped lens.

14. An electrophoresis apparatus according to claim 9, wherein said one or more laser beams incident on the sieving matrix are collimated by a collimator located before the first waveguiding unit.

15. An electrophoresis apparatus according to claim 14, wherein said collimator is a convex-shaped lens.

16. An electrophoresis apparatus according to claim 9, wherein said at least one laser source comprises means for generating a plurality of laser beams.

17. An electrophoresis apparatus according to claim 16, wherein each one of said plurality of said laser beams is of a substantially different wavelength.

18. A plate including a sieving matrix for electrophoresis of a sample,
said plate including an optical waveguide array extending in the width direction of the plate within the sieving matrix for focusing a laser beam,
said optical waveguide array comprising a plurality of convex shaped lenses extending along said array,
said array being characterized by being aligned with respect to a reference direction such as to enable the laser beam incident on the sieving matrix along said reference direction to be maintained focused and well-confined along said reference direction within any desired length of interaction along the width of said sieving matrix.

19. A generally planar plate extending along x and y directions, wherein the x direction is the width direction, and the y direction is the length direction, said plate including a sieving matrix for electrophoresis of a sample,
said plate including an optical waveguide array within the sieving matrix having a plurality of gel lanes extending in the y direction,
said optical waveguide array being aligned in the x direction such as to enable a laser beam incident on the sieving matrix along the x direction to be maintained focused and well-confined along said x direction within any desired length of interaction along the width of said sieving matrix.

* * * * *